(12) United States Patent
Hendler et al.

(10) Patent No.: US 6,541,613 B2
(45) Date of Patent: Apr. 1, 2003

(54) ISOFLAVONE DERIVATIVES

(75) Inventors: Sheldon S. Hendler, La Jolla, CA (US); Jan Zielinski, San Diego, CA (US)

(73) Assignee: Uyrex Corporation, La Jolla, CA (US)

( * ) Notice: Subject to any disclaimer, the term of this patent is extended or adjusted under 35 U.S.C. 154(b) by 0 days.

(21) Appl. No.: 09/737,895

(22) Filed: Dec. 15, 2000

(65) Prior Publication Data

US 2002/0111466 A1 Aug. 15, 2002

(51) Int. Cl.[7] ............. C07D 311/04; C07D 311/74; C07H 15/02
(52) U.S. Cl. .................. 536/8; 549/402; 549/403; 549/220
(58) Field of Search ............... 549/220, 402, 549/403; 536/8

(56) References Cited

U.S. PATENT DOCUMENTS 5,550,152 A * 8/1996 Koch et al. ............... 514/458
5,679,806 A    10/1997 Zheng et al. ............. 549/403

* cited by examiner

*Primary Examiner*—Joseph K. McKane
*Assistant Examiner*—Andrea D. Small
(74) *Attorney, Agent, or Firm*—Rutan & Tucker; Robert D. Fish

(57) ABSTRACT

Isoflavones are modified by esterification at one or more of the C4', C5, C6, and C7 positions to promote bioavailability, and especially to enhance solubility over the corresponding unesterified isoflavones. Preferred modifications produce a carboxylic acid hemiester or a phosphate ester which is biologically hyrolyzable. Preferred starting isoflavones are genistin and daidzin, and still more preferably comprises an aglycone form such as genistein or daidzein. Esterified isoflavones may be employed therapeutically or prophylactically for a variety of conditions, provided as a dietary supplement, or added to natural or processed food-stuffs.

7 Claims, 1 Drawing Sheet

ISOFLAVONE DERIVATIVES

FIELD OF THE INVENTION

The field of the invention is isoflavones.

BACKGROUND OF THE INVENTION

The isoflavones are a group of naturally occurring plant compounds having the aromatic heterocyclic skeleton of flavan. Soybeans are the most common and well known source of isoflavones, reported to contain the isoflavones, daidzin, genistin, glycitin, 6"-dadidzin-O-acetyl, 6"-O-acetyl genistin, 6"-O-malonyl daidzin, and 6"-O-malonyl genistin. (see U.S. Pat. No. 5,679,806 to Zheng et al., (October 1997) incorporated herein by reference). Isoflavones are present in processed soy foods as well, including miso and soy sauce. Legumes, lupine, fava bean, kudzu and psoralea may also be important sources. The existence of isoflavones in Pueraria has long been known, with the roots of Pueraria containing several isoflavone compounds, such as daidzin, and puerarin.

Isoflavones are known in aglucone forms, as well as 7-acetylated and 7-substituted glycosides. Especially important isoflavones in aglucone form include daidzein, genistein, and glycitein. Especially important isoflavones in 7-glycoside form include daidzin, genistin, and glycitin. Genistein is also known to occur naturally as a 4'-glucoside (sophoricoside), and a 4'-methyl ether (biochanin A).

Isoflavones in general, and genistein in particular, have structural similarities to that of certain human estrogens, and such compounds are said to have estrogenic activity. Isoflavones are also said to have other useful biological and pharmacological activities, including antiangiogenic, antihemolytic, antiischemic, antileukemic, antimitogenic, antimutagenic, antioxidant, fungicidal, pesticidal, MAO-inhibition, phytoalexin, and tyrosine kinase inhibition activities (1).

The anticancer effects of genistein are of particular interest. Genistein may exert antitumor effects in part by inhibiting angiogenesis, i.e., reducing formation of vasulature and blood flow to the tumor. Its affinity to estrogenic sites in the vicinity of cancer cells may also inhibit tumor growth. As a well-known inhibitor of the enzyme tyrosine kinase, genistein may also inhibit energy and signaling pathways in tumors. Examples of research are described in references 4 and 5.

Genistein and other isoflavones are also said to be important contributors to bone health, resulting at least in part from the ability of these compounds to inhibit protein kinase activity, and thereby inhibit osteoclast cell activity. The isoflavones are especially attractive in this regard because they generally have a low toxicity relative to many other known protein kinase inhibitors. Examples of research along these lines are described in references 6 and 7. Citations for still other research articles describing beneficial effects of isoflavonoids are set forth as references.

Because of its many beneficial effects, enriched sources of genistein are marketed to consumers around the world in a wide variety of nutritional supplements. Many of the health benefits of soy products are ascribed to the presence of genistein.

Unfortunately genistein and other isoflavones are very insoluble in water. See, for example, descriptions of genistein, genistin, biochanin A, and sophoricoside in the Merck Index (3). The insolubility of the isoflavones complicates their formulation into foodstuffs and cosmetics, many of which are aqueous-based systems. Low solubility is also frequently an impediment to efficient bioavailability in orally administered products. Low solubility is a particularly serious impediment to formulation of intravenous medications, which are most often delivered in aqueous media.

Thus, there is a continuing need to provide isoflavones in forms which have increased bioavailability, especially enhanced aqueous solubility relative to the unmodified compounds, while retaining the active properties of such unmodified compounds.

SUMMARY OF THE INVENTION

Methods and compositions of the present invention provide increased bioavailability of isoflavones by converting a starting isoflavone into a pro-compound. This is preferably accomplished by attaching a polar (solubilizing) leaving group which can be readily hydrolyzed under physiologic conditions to produce the starting isoflavone.

In preferred embodiments, an alcohol functionality of an isoflavone is esterified using a carboxylic acid group or a phosphoric acid group. This yields a carboxylic acid hemiester or a phosphate ester. In general, fluids of the digestive and absorptive gastrointestinal tract, other acids, and various enzymes are capable of hydrolyzing the esterified isoflavone to the starting isoflavone.

In another aspect of the invention, the starting isoflavone preferably comprises a natural isoflavone, more preferably comprises genistin or daidzin, and still more preferably comprises an aglycone form such as genistein or daidzein.

In still other aspects of the invention, the pro-compounds may advantageously be employed therapeutically or prophylactically for a variety of conditions, provided as a dietary supplement, or added to natural or processed foodstuffs. Thus, the pro-compounds may be used as pro-drugs or pro-nutrients.

Various objects, features, aspects and advantages of the present invention will become more apparent from the following detailed description of preferred embodiments of the invention.

DETAILED DESCRIPTION

Figure 1:
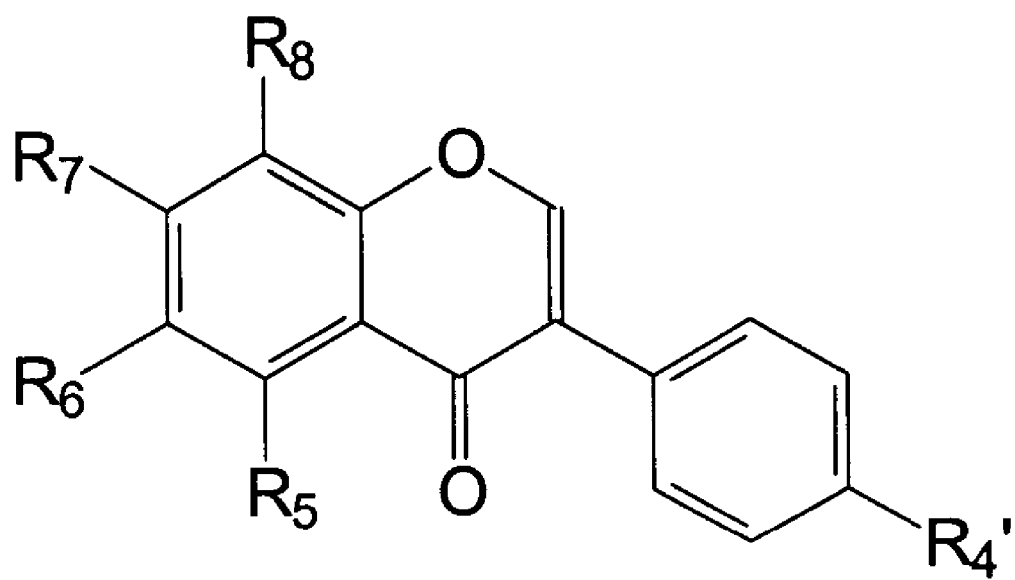
FIG. 1 is a structural representation of a generalized isoflavone.

FIG. 1 depicts a generalized isoflavone.

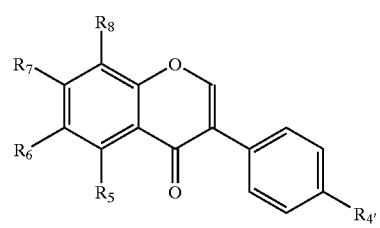

FIG. 1

Using this structure as a reference, known isoflavones include the following (where the 6"position is on the glucose ring):

| Isoflavone | $R_8$ | $R_7$ | $R_6$ | $R_5$ | $R_4'$ |
| --- | --- | --- | --- | --- | --- |
| daidzin | H | O-glucose | H | H | OH |
| genistin | H | O-glucose | H | OH | OH |
| glycitein | H | OH | OMe | H | H |
| puerarin | glucose | OH | H | H | H |
| 6"-O-acetyl daidzin | H | O-acetyl glucose | H | H | OH |
| 6"-O-acetyl genistin | H | O-acetyl glucose | H | OH | OH |
| 6"-O-malonyl daidzin | H | O-malonyl glucose | H | H | OH |
| 6"-O-malonyl genistin | H | O-malonyl glucose | H | OH | OH |
| genistein | H | OH | H | OH | OH |
| daidzein | H | OH | H | H | OH |
| glycitin | H | O-glucose | OMe | H | H |

It is now contemplated that a natural or modified isoflavone may be esterified to provide a pro-compound having increased bioavailability, and in particular enhanced aqueous solubility relative to the unesterified isoflavone. In preferred embodiments one or more of $R_7$, $R_6$, $R_5$ and $R_4'$ comprise ZOOO— or $ZPO_4$—, where Z is selected from the group consisting of a straight or branched aliphatic chain, including an alkyl, alkenyl, alkynyl, alkoxyalkyl, alkylthioalkyl, aminoalkyl group, including substituted derivatives of such groups, a substitute or non-substituted cycloalkyl, and an aromatic group, including aryl, aralkyl, or alkylaryl, and substituted derivatives such as where a ring contains one or more nitrogen, sulfur, oxygen, phosphorous or silicon heteroatoms. Such compounds are considered herein to be esterified isoflavones in which an isoflavones is modified by esterification in at least one of the C4', C5, C6, and C7 positions.

To clarify further, it is contemplated that Z may comprise hydrogen; hydroxyl; cyano; nitro; halo; alkyl such as methyl, ethyl, butyl, pentyl, octyl, nonyl, tert-butyl, neopentyl, isopropyl, sec-butyl, dodecyl and the like, alkenyl such as 1-propenyl, 4-butenyl, 1-pentenyl, 6-hexenyl, 1-heptenyl, 8-octenyl and the like; alkoxy such as propoxy, butoxy, methoxy, isopropoxy, pentoxy, nonyloxy, ethoxy, octyloxy, and the like; alkanoyl such as butanoyl, pentanoyl, octanoyl, ethanoyl, propanoyl and the like; arylamino and diarylamino such as phenylamino, diphenylamino and the like; alkylsulfinyl, alkylsulfonyl, alkylthio, arylsulfonyl, arylthio, and the like, such as butylthio, neopentylthio, methylsulfinyl, benzylsulfinyl, phenylsulfinyl, propylthio, octylthio, nonylsulfonyl, octylsulfonyl, methylthio, isopropylthio, phenylsulfonyl, methylsulfonyl, nonylthio, phenylthio, ethylthio, bezylthio, phenethylthio, sec-butylthio, naphthylthio and the like; alkoxycarbonyl such as methoxycarbonyl, ethoxycarbonyl, butoxycarbonyl and the like; alkyl amino and dialkylarnino such as dimethylamino, methylamino, diethylamino, ethylamino, dibutylamino, butylamino and the like; cycloalkyl such as cyclohexyl, cyclopentyl, cyclooctyl, cycloheptanyl and the like; alkoxyalkyl such as methoxymethylene, ethoxymethylene, butoxymethylene, propoxyethylene, pentoxybutylene and the like; arylalkylarnino such as methylphenylamino, ethylphenylamino and the like; aryloxyalkyl and aryloxyaryl such as phenoxyphenylene, phenoxymethylene and the like; and various substituted alkyl and aryl groups such as 1-hydroxybutyl, 1-aminobutyl, 1-hydroxylpropyl, 1-hydroxypentyl 1-hydroxyoctyl, 1-hydroxyethyl, 2-nitroethyl, trifluoromethyl, 3,4-epoxy-butyl, cyanomethyl, 3-chloropropyl, 4-nitrophenyl, 3-cyanophenyl, 1-hydroxymethyl, and the like; hydroxyl terminated alkyl and aryl groups such as, 2-hydroxy ethyl, 4-hydroxy butyl and 4-hydroxy phenyl; sulfonic, sulfuric, carboxylic, phosphoric and phosphoric acid terminated alkyl and aryl groups such as ethylsulfonic acid, propylsulfonic acid, butylsulfonic acid, phenylsulfonic acid, and the corresponding carboxylic and phosphoric acids and derivatives of said sulfonic, carboxylic and phosphoric acids as for example salts, esters and the like.

Of course, those skilled in the art will appreciate that higher solubility in aqueous environments is generally preferred over lower solubility. Thus, where $R_7$, $R_6$, $R_5$ or $R_4'$ comprise ZOOO—, Z is advantageously selected to have a polar group, and any alkyl segment is advantageously selected to be small. Among the dicarboxylic acid groups, hemisuccinate is by far the most common, useful and biocompatible group, and is specifically contemplated for this purpose. Glutarate and adipate are also preferred.

Where $R_7$, $R_6$, $R_5$ and $R_4'$ comprise $ZPO_4$—, a $(OH)_2PO_2$ ester is preferred because it has two polar groups, is a good solubilizer, and has high biological compatibility. Any additions to the $PO_4$ (such as $(RO)_2PO_2$—) are contemplated to generally reduce aqueous solubility, and are therefore disfavored.

With respect to complexes, it is contemplated to employ metal salts of the esterified isoflavones, especially Li+, Na+, K+, Mg++ and ammonium salts, including NH4+ and low molecular weight mono- or polyalkylammonium.

EXAMPLES

By way of example, and not of limitation, several embodiments of the inventive subject matter have been prepared and characterized. These examples all fall within the group of pro-compounds where at least one of $R_7$, $R_6$, $R_5$ and $R_4'$ is $H_2PO_4$—, and HOOC—$(CH_2)$x—COO— where x=2, 3, or 4. These new phosphate esters and hemiesters are all water soluble and readily hydrolyzed. They are also stable. In aqueous solutions of the exemplified compounds, for example, hydrolysis occurs to the extent of less than 1% per day, when stored at pH 7.4 and 37° C. Dry formulations of the same compounds appear to be indefinitely stable.

Example 1

Mixed Phosphate Esters of Genistein

A solution of genistein (135 mg, 0.5 mmole) and di-tert-butyl phosphoramidite (330 ul, 1.0 mmole) in DMF (1 ml) was stirred under argon while 1H-tetrazole (210 mg in 0.5 ml of DMF; 3.0 mmole) was added dropwise. After a few minutes, the solution was cooled to −20° C., then a solution of m-chloroperbenzoic acid (260 mg in 0.5 ml of methylene chloride, 1.5 mmole) was added dropwise. After warming to room temperature, the mixture was diluted threefold with ethyl acetate, then washed with 10% sodium metabisulfie and 10% sodium bicarbonate. A wash with 5% sodium carbonate removed a trace of unreacted genistein.

The ethyl acetate solution, containing the butyl esters of the genistein phosphates, was washed with 1M HCl and dried over sodium sulfate. After removal of the solvent in vacuo, the residue was treated with 30% TFA in acetic acid for 90 minutes at room temperature. The solvents were removed in vacuo, and the residue was taken up in ethanol and neutralized with sodium hydroxide to pH 5.5. Removal of the solvent in vacuo left a mixture of sodium salts of genistein phosphates, 145 mg.

HPLC analyses were performed using a Chrompack Intersil C8 column, 4.6×250 mm. The solvent was a mixture of 25% acetonitrile and 75% 0.1M diammonium phosphate, pH 2.5, at a flow rate of 1 ml/min. Detection was by UV at a wavelength of 260 nm.

HPLC analysis of the phosphate mixture showed approximately equal amounts of the 4'-phosphate, the 7-phosphate and the 4', 7- diphosphate, and only a small amount of the 5-phosphate.

Example 2

Genistein-7-phosphate a) Genistein-7-tosylate: p-Toluenesulfonyl chloride (540 mg, 2.8 mmoles) was added during 4 hours to a stirred mixture of genistein (730 mg, 2.7 mmoles) and potassium carbonate (2 g) in 25 ml of acetone. After stirring overnight, the mixture was poured into brine and extracted with ethyl acetate. The extract was evaporated under vacuum, and the residue chromatogrammed through silica gel with dichloromethane and chloroform. Crystallization from methanol yielded 920 mg (80.2% yield) of genistein-7-tosylate. The proton magnetic resonance spectrum was consistent with the expected structure.

4',5-Di(methoxymethyl)-genistein-7-tosylate: Chloromethyl methyl ether (90 ul, 1.12 mmoles) was added to a solution of genistein-7-tosylate (106 mg, 0.25 mmoles) and diisopropylethylamine (200 ul, 1.15 mmoles) in 0.6 ml of dioxane, under argon atmosphere, and stirred overnight. The mixture was poured into brine, extracted with ethyl acetate, and chromatogrammed through silica gel with dichloromethane. Crystallization from methanol yielded 115 mg (90% yield) of 4',5-Di(methoxymethyl)-genistein-7-tosylate. The proton magnetic resonance spectrum was consistent with the expected structure.

c) 4',5-Di(methoxymethyl)-genistein: Potassium carbonate (700 mg) in water (5 ml) was added to a solution of 4',5-di(methoxymethyl)-genistein-7-tosylate (600 mg, 1.17 mmoles) in 15 ml methanol under argon, and stirred overnight. The mixture was poured into brine, extracted with ethyl acetate, and recrystallized from methanol. The yield of 4',5-Di(methoxymethyl)-genistein was 344 mg (82%).

The electrospray mass spectrum in negative mode showed ion m/z 357[M-1] which confirmed the expected molecular weight of 358. The proton and carbon magnetic resonance spectra were consistent with the expected structure.

d) Genistein-7-phosphate: 1H-Tetrazole (120 mg, 1.7 mmoles) was added to a solution of di-tert-butyl-diethylphosphoramidite (180 ul, 0.64 mmoles) and 4',5-di(methoxymethyl)-genistein (200 mg, 0.56 mmoles) in 1.5 ml of N,N-dimethylacetamide under argon. After 10 minutes at room temperature, the mixture was cooled to −40° C., and a solution of m-chloroperbenzoic acid (130 mg, 0.75 mmoles) in dichloromethane was added rapidly. After warming to room temperature, the mixture was diluted with ether and washed with brine containing sodium bicarbonate. The solvent was removed, and the residue treated with 40% trifluoroacetic acid in acetic acid for 30 minutes. The volatile acids were removed under vacuum, and the residue dissolved in 2-propanol (4 ml) containing 0.2 ml 6N HCl and left overnight. The mixture was poured into brine and extracted with ethyl acetate. The solvent was removed, and the residue was dissolved in ethanol (3 ml) and adjusted to pH 5.5 with NaOH. After evaporation, the residue was crystallized from ethanol, yielding 155 mg (75% yield) of genistein-7-phosphate as the sodium salt.

The electrospray mass spectrum in negative mode showed ion m/z 349[M-1] which confirmed the expected molecular weight of 350. The nuclear magnetic resonance spectra were consistent with the expected structure.

Example 3

Mixed Hemisuccinate Esters of Genistein

A solution of genistein (135 mg, 0.5 mmole) in 2.0 ml of pyridine was stirred at room temperature while succinic anhydride (100 mg, 1.0 mmole) was added in several portions. After stirring overnight at room temperature, the solvent was removed in vacuo. The gummy residue was taken up in water, adjusted to pH 3.0, and extracted three times with ethyl acetate. The ethyl acetate extracts were washed with water, then evaporated to dryness in vacuo. The crude mixture of mixed hemisuccinic acid esters weighed 205 mg.

Thin layer chromatography of the product showed principally the presence of mixed mono- and disuccinate esters of genistein. The product was completely soluble in phosphate buffer at pH 7.

Example 4

Genistein-7-hemisuccinate

To a solution of 4',5-Di(methoxymethyl)-genistein (see example 2c) (100 mg, 0.28 mmole) in 1.5 ml of pyridine was added succinic anhydride (50 mg, 0.5 mmole) with stirring at room temperature. After stirring overnight, the solvent was removed in vacuo. The residue was taken up in water containing one drop of glacial acetic acid, and again evaporated to dryness in vacuo. The residue was chromatogrammed through silica gel with dichloromethane and ethyl acetate. The yield of the 7-hemisuccinic ester of 4',5-di(methoxymethyl)-genistein was 102 mg (78%). The product was dissolved in 2-propanol (3 ml) containing 0.2 ml 6N HCl and left overnight. The solution was evaporated to dryness. The residue taken up in 1 ml of ethyl acetate and crystallized by the addition of hexane. The yield of genistein-7-hemisuccinate was 52 mg (50%).

Example 5

Non-enzymatic Hydrolysis of Genistein Esters

HPLC analysis was conducted using a Partisil ODS-3 column (9.5×250 mm), with methanol as the mobile phase, and UV detection at 260 nm.

A solution of genistein-7-phosphate (2.5 mg) in 5 ml of phosphate-buffered saline (0.1 M) at pH 7.4 was incubated at 37° for 10 days. Analysis by HPLC showed that absence of free genistein.

A solution of genistein-7-hemisuccinate (2.5 mg) in 5 ml of phosphate-buffered saline (0.1 M) at pH 7.4 was incubated at 37° for 10 days. Analysis by HPLC showed a conversion of about 4% of the hemisuccinate ester to free genistein.

Example 6

Hydrolysis of Genistein-7-phosphate by Various Enzymes and Biological Media

In each of these experiments, free genistein was extracted with a 1:1 mixture of ethyl acetate and hexane, then analyzed by HPLC under the conditions described in example 5.

a) In human serum (Sierra Biologicals) at 37° C., the half-life for hydrolysis to free genistein was about 5 hours.

b) In human blood (Sierra Biologicals) at 37° C., the half-life for hydrolysis to free genistein was about 6 hours.

c) In rat blood (Sierra Biologicals) at 37° C., the half-life for hydrolysis to free genistein was about 30 minutes.

d) In human serum (Sierra Biologicals) at 37° C., the half-life for hydrolysis to free genistein was about 5 hours.

e) In alkaline phosphatese type VII-S at 37° C., the initial rate of hydrolysis to free genistein was 0.08% per minute.

This enzyme is from bovine intestinal mucosa (Sigma cat no. P5521). 0.5 DEA units were dissolved in 1.0 ml of 0.1M glycine buffer pH 10.4, and the initial substrate concentration was 1.07 mM.

f) In alkaline phosphatese type XXIV at 37° C., the initial rate of hydrolysis to free genistein was 0.05% per minute.

This enzyme is from human placenta (Sigma cat no. P3895). 0.1 glycine units were dissolved in 1.0 ml of 0.1M glycine buffer pH 10.4, and the initial substrate concentration was 1.07 mM.

Uses

It is contemplated that esterified isoflavones will be readily converted to free isoflavone in biological media such as gastrointestinal fluid and blood. Among other things, gastrointestinal fluids often have enzymes and sufficiently high pH to hydrolyze ester bonds, and blood generally contains enzymes such as phosphatases and esterases which can hydrolyze phosphate ester and carboxylate ester bonds.

Contemplated uses of esterified isoflavones include any presently known or later discovered uses for isoflavones or isoflavonoids. Among other things, it is contemplated that esterified isoflavones can be administered to (which term is used herein to include "taken by") a person for any of the beneficial effects for which a natural isoflavonoid is thought to be advantageous. This specifically includes any of the effects listed above or described in any of the literature cited herein, and includes uses where the desired effect is antiangiogenic, antihemolytic, antiischemic, antileukemic, antimitogenic, antimutagenic, antioxidant, fungicidal, pesticidai, MAO-inhibition, phytoalexin, and tyrosine kinase inhibition. It is especially contemplated that esterified isoflavones can be used to treat osteoporosis and other symptoms of estrogen deficiency in postmenopausal women. Also, it is contemplated that the compounds of the present invention can be used to prevent osteoporosis and consequent fractures that result from osteoporosis, which are major contributors to morbidity and mortality in the elderly. Still further, it is contemplated that esterified isoflavones can be used prophylactically to provide UV protection and in other ways to improve general skin health, to stimulate the immune system, and to reduce undesirable effects of oxidation (i.e., provide antioxidant benefits).

Those skilled in the art will recognize that esterified isoflavones may be employed in many different ways. When taken orally, esterified isoflavones may be incorporated into food or beverage material, for nutritional, therapeutic, prophylactic value, or any combination of these. Esterified isoflavones may also be administered by any appropriate form of in vivo delivery, which is defined herein to include oral, intravenous, subcutaneous, intraperitoneal, intrathecal, intramuscular, intracranial, inhalational, topical, transdermal, suppository (rectal), pessary (vaginal), administration and the like. Thus, delivery may occur through foods, pills, capsules or liquids as a nutritional supplement, or as a pharmaceutical By way of example, it is contemplated that compounds according to the present invention can be administered alone, or formulated in admixture with a pharmaceutically acceptable carrier. For example, the compounds of the present invention can be administered orally as pharmacologically acceptable salts. Because preferred compounds of the present invention are relatively water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. It is also well within the ordinary skill of the art to modify the route of administration and dosage regimen of a particular compound in order to manage the pharmacokinetics of the present compounds for maximum beneficial effect in patients. One of ordinary skill in the art will also take advantage of favorable pharmacokinetic parameters of the pro-drug forms, where applicable, in delivering the present compounds to a targeted site within the host organism or patient to maximize the intended effect of the compound.

In addition, compounds according to the present invention may be administered alone or in combination with other agents for the treatment of the above mentioned diseases or conditions. Combination therapies according to the present invention may comprise the administration of at least one compound of the present invention or a functional derivative thereof, and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

Thus, specific embodiments and applications of esterified isoflavones have been disclosed. It should be apparent, however, to those skilled in the art that many more modifications besides those already described are possible without departing from the inventive concepts herein. The inventive subject matter, therefore, is not to be restricted except in the spirit of the appended claims.

References: (Incorporated Herein by Reference)
1. Phytochemical Database of the USDA Agricultural Research Service, Stephen M. Beckstrom-Sternberg & James A. Duke, Internet address: www.ars-grin.gov/~ngrlsb/
2. A comparative survey of leguminous plants as sources of the isoflavones, genistein and daidzein: implications for human nutrition and health. Kaufman P B; Duke J A; Brielmann H; Boik J; Hoyt J E, J Altern Complement Med, 1997, vol. 3 (1) p7–12.

3. The Merck Index, 12th Edition (1996), Merck & Co., Inc, Whitehouse Station, N.J., genistein, genistin, biochanin A: entry no. 4395 sophoricoside: entry no. 8867
4. Genistein inhibits growth of B16 melanoma cells in vivo and in vitro and promotes differentiation in vitro. Record I R; Broadbent J L; King R A; Dreosti I E; Head R J; Tonkin A L. Int. J. Cancer, 1997, vol 72 (5) p860–4
5. Genistein inhibits proliferation and in vitro invasive potential of human prostatic cancer cell lines. Santibanez J F; Navarro A; Martinez J. Anticancer Res, 1997, vol 17 (2A) p1199–204
6. Action of genistein and other tyrosine kinase inhibitors in preventing osteoporosis. Presented by H. C. Blair at: Second International Symposium on the Role of Soy in Preventing and Treating Chronic Disease, Sep. 15–18, 1996, Brussels, Belgium.
7. Inhibitory effect of genistein on bone resorption in tissue culture. Yamaguchi M; Gao Y H. Biochem Pharmacol, 1998, vol 55 (1) p71–6.
8. Effect of soybean phytoestrogen intake on low density lipoprotein oxidation resistance. Tikkanen M J et al., Proc Natl Acad Sci (USA), March 1998, vol 95 (6), p3106–10.
9. Genistein, the dietary-derived angiogenesis inhibitor, prevents LDL oxidation & protects endothelial cells from damage by atherogenic LDL. Kapiotis S, et al. Arterioscler Thromb Vasc Biol (US), November 1997, vol 17(11), p2868–74.
10. Effect of structurally related flavones/isoflavones on hydrogen peroxide production and oxidative DNA damage in phorbol ester-stimulated HL-60 cells. Giles D, Wei H. Nutr Cancer (US), 1997, vol 29(1), p77–82.
11. Antioxidant activity of phytoestrogeneic isoflavones. Ruiz-Larrea M B, et al. Free Radic Res. (Switzerland), January 1997, vol 26(1), p63–70.
12. Antioxidant and antipromotional effects of the soybean isoflavone genistein. Wei H., et al. Proc Soc Exp Biol Med (US), January 1995, vol 208(1), p124–30.
13. Mechanism of antioxidant action of pueraria glycoside (PG)-1 (an isoflavonoid) and mangiferin (a xanthonoid). Sato T, et al., Chem Pharm Bull (Japan), March 1992, vol 40 (3) p721–4.
14. Inhibition of UV light- and Fenton reaction-induced oxidative DNA damage by the soybean isoflavone genistein. Wei H, et al. Carcinogenesis (England), January 1996, vol 17(1) p73–7.
15. Evolution of the health benefits of soy isoflavones. Barnes S. Proc Soc Exp Biol Med (US) March 1998, vol 217 (3), p386–92.
16. Natural and synthetic isoflavones in the prevention and treatment of chronic diseases. Brandi M L, Calcif Tissue Int (US) 1997, 61 Suppl 1, pS5–8.
17. Effect of isoflavones genistein and daidzein in the inhibition of lung metastasis in mice induced by B16F-10 melanoma cells. Menon L G, et al. Nutr Cancer (US), 1998, vol 30 (1) p74–7.
18. Enhancement of immune function in mice fed high doses of soy daidzein. Zhang R., et al.; Nutr Cancer (US), 1997, vol. 29(1) p24–8.
19. Inhibition of N-methyl-N-nitrosourea-induced mammary tumors in rats by the soybean isoflavones. Constantinou A., Anticancer Res (GREECE) November-December 1996, vol. 16(6A), p3293–8.
20. Kudzu root: an ancient Chinese source of modern antidipsotropic agents. Keung W. M., et al.; Phytochemistry (US), February 1998, vol. 47(4), p499–506.
21. Isoflavonoid compounds extracted from Pueraria lobata suppress alcohol preference in a pharmacogenetic rat model of alcoholism. Lin R. C., et al.; Alcohol Clin Exp Res (US), June 1996, vol. 20(4), p659–63.

What is claimed is:

1. A compound having the structure:

FIG. 1 wherein $R_7$, $R_6$, $R_5$ and $R_4'$ are independently selected from the group consisting of H, OH, OMe, glucose, O-glucose, O-acetyl glucose, O-malonyl glucose, ZOOO— and $ZPO_4$—;

with the proviso that at least one of $R_7$, $R_6$, $R_5$ and $R_4'$ is ZCOO— or $ZPO_4$—, where Z is selected from the group consisting of a straight or branched alkyl, alkenyl, alkynyl, alkoxyalkyl, alkylthioalkyl, or aminoalkyl, a substituted or non-substituted cycloalkyl, an aryl, aralkyl, or alkylaryl, and a substituted cycloalkyl where at least one ring contains one or more of a nitrogen, sulfur, oxygen, phoshorous or silicon heteroatom in the at least one ring; and wherein $R_8$ is H or glucose.

2. The compound of claim 1 wherein $R_7$ is glucose.

3. The compound of claim 1 wherein $R_7$ is glucose and $R_5$ is OH.

4. The compound of claim 1 wherein $R_7$ is glucose and $R_4'$ is H.

5. The compound of claim 1 wherein the esterified compound having at least one of ZCOO— or $ZPO_4$— has a solubility in water that is greater than the solubility of a corresponding compound without the at least one of ZCOO— or $ZPO_4$— in water at 25° C.

6. The compound of claim 1 wherein the compound is a carboxylic acid hemiester.

7. The compound of claim 1 wherein the compound is a phosphate ester.

* * * * *

UNITED STATES PATENT AND TRADEMARK OFFICE
CERTIFICATE OF CORRECTION

PATENT NO. : 6,541,613 B2
DATED : April 1, 2003
INVENTOR(S) : Sheldon S. Hendler and Jan Zielinski It is certified that error appears in the above-identified patent and that said Letters Patent is hereby corrected as shown below:

<u>Title page,</u>
Item [73], Assignee, replace "Uyrex Corporation" with -- Vyrex Corporation --.

Signed and Sealed this

Twenty-first Day of June, 2005

JON W. DUDAS
*Director of the United States Patent and Trademark Office*